United States Patent [19]

Philapitsch et al.

[11] Patent Number: 4,608,254

[45] Date of Patent: Aug. 26, 1986

[54] METHOD FOR THE PRODUCTION OF THERAPEUTICALLY ADMINISTRABLE PLASMA DERIVATIVES FILLED IN FINAL CONTAINERS

[75] Inventors: Anton Philapitsch, Ebenfurt; Yendra Linnau, Vienna, both of Austria

[73] Assignee: Immuno Aktiengesellschaft fur chemisch-medizinische Produkte, Vienna, Austria

[21] Appl. No.: 587,223

[22] Filed: Mar. 7, 1984

[30] Foreign Application Priority Data

Mar. 16, 1983 [AT] Austria ................................. 932/83

[51] Int. Cl.$^4$ ............................................. A61K 35/16
[52] U.S. Cl. .................................................... 424/101
[58] Field of Search ......................................... 424/101

[56] References Cited

PUBLICATIONS van der Starre et al—New England J. of Med. (May 31, 1979) p. 1276.
U.S. Pharmacopeia—20th revision, Jul. 1, 1980, "Plasma Protein Fraction" monograph.
Chem. Abst. Gen. Subj. Index, 10th Coll. (1977–1981) p. 4992GS.
Alving, B. M. et al, "Hypotension Associated with Prekallikrein Activator (Hageman–Factor Fragments) in Plasma Protein Fraction." *The New England Journal of Medicine*, vol. 299, No. 2 (1978), pp. 66–70.
Snape, T. J., Griffin, D., Vallet, D. L. and Wesley, E. D., "The Assay of Prekallikrein Activator in Human Blood Products." *Develop. Biol. Standard*, vol. 44 (1979), pp. 115–120.
Schreiber, A. D., Kaplan, A. P. and Austen, K. F., "Inhibition by $Cl_1^{NH}$ of Hageman Factor Fragment Activation of Coagulation, Fibrinolysis, and Kinin Generation." *The Journal of Clinical Investigation*, vol. 52 (1973), pp. 1402–1409.
Vogelaar, E. F., Brummelhuis, H. G. J. and Krijnen, H. W., "Contributions to the Optimal Use of Human Blood." *Vox Sang.*, vol. 26 (1974), pp. 118–127.
Trautschold, I., "Assay Methods in the Kinin System." Handbook of Experimental Pharmacology, vol. 25 (1970), pp. 52–59.

*Primary Examiner*—Sam Rosen
*Attorney, Agent, or Firm*—Burns, Doane, Swecker & Mathis

[57] ABSTRACT

There is disclosed a method for the production of therapeutically administrable plasma derivatives filled in final containers, which are free of prekallikrein activator, hypotensively active constituents and other undesired pharmacologically active substances, of plasma or plasma crude fractions by stepwise enrichment of the plasma proteins, sterile filtration and optionally virus inactivation. In order to make available such plasma fractions that do not develop pharmacologically negative side effects when applied and are producible with an improved activity and yield, $C_1$-esterase inhibitor is added during the production process of the plasma derivative, yet prior to its filling into final containers.

5 Claims, No Drawings

METHOD FOR THE PRODUCTION OF THERAPEUTICALLY ADMINISTRABLE PLASMA DERIVATIVES FILLED IN FINAL CONTAINERS

The invention relates to a method for the production of therapeutically administrable plasma derivatives filled in final containers, which are free of prekallikrein activator, hypotensively active constituents and other undesired pharmacologically active substances, in particular for the production of albumin, globulin and coagulation-factor preparations, of plasma or plasma crude fractions by stepwise enrichment of the plasma proteins, sterile filtration as well as, if desired, by virus inactivation.

The administration of blood derivatives of the type mentioned may lead to undesired side reactions in patients, in particular to a spontaneous blood pressure decrease, which may reach dangerous extents. This hypotensive activity of the preparations is assumed to go back to a content of proteins that can be eliminated during plasma fractionation only partially or with high losses of the desired active substances (cf. e.g. The New England Journal of Medicine, "Hypotension Associated with Prekallikrein Activator (Hagemann-Factor Fragments) in Plasma Protein Fraction", Vol. 299, Alving et al., July 1978, pp. 66 to 70). The undesired substances with hypotensive effects have been classified as fragments of the coagulation factor XII (F $XII_f$) on the one hand, their activity having been denoted as "prekallikrein activator activity" (PKKA); and by substances which, as impurities in the preparations, may cause pharmacologically undesired side reactions and lead to reactions irrespective of PKKA activity, on the other hand. The in vitro assaying of PKKA activity usually is realized via the determination of kallikrein (KK), which is generated from an inactive prestage (prekallikrein) after addition of F $XII_f$. Kallikrein cleaves tripeptide-based chromogenic substrate. The chromophore group liberated is photometrically measured (cf. Develop. biol. Standard, Vol. 44, pp. 115 to 120, "The Assay of Prekallikrein-Activator in Human Blood Products", T. J. Snape et al.). The content of PKKA in the test material is indirectly concluded and related to an International Standard (Reference PKA Standard Lot 2 of the Bureau of Biologics, Bethesda, U.S.A.).

Since side reactions depend not only from the PKKA content, further test methods suggesting in vivo reactions have been applied to investigate blood derivatives. One of these methods is the kallikrein burst test, with which the sample is added to human plasma, the spontaneously occurring kallikrein liberation in the plasma being photometrically measured with chromogenic substrate S 2302 (Kabi) via the liberation of p-nitroanilide from the chromogenic substrate. This kallikrein liberation from plasma, as opposed to PKKA-induced kallikrein liberation from the inactive pre-stage, is to be assessed differently, since no kinetics is involved, but it occurs spontaneously within the first minutes, disappearing again.

A further possibility to investigate into pharmacological side reactions resides in the contraction at the isolated ileum of guinea pigs. By the samples to be tested, substances are liberated in human plasma that lead to a contraction at the isolated ileum.

It is known that the activity of the prekallikrein activator may be reduced or suppressed, if an inhibitor, i.e. $C_1$-esterase inhibitor ($C_1INA$) is present. This $C_1$-esterase inhibitor has been described in literature also as F $XII_f$-inhibitor (cf. The Journal of Clinical Investigation, Vol. 52, June 1973, pp. 1402 to 1409, A. D. Schreiber et al.). The inhibitor is prepared from human plasma according to known modes of operation (Vox. Sang. 26: 118 to 127 (1974), "Contributions to the Optimal Use of Human Blood", E. F. Vogelhaar et al.).

It has already been proposed to add $C_1$-esterase inhibitor to a stable plasma protein solution (PPL) immediately before being applied to the patient. This ready-made applicable preparation has an ionic strength of 130 to 160 mequ/l. A disadvantage of this method, however, is that the $C_1$-esterase inhibitor is only insufficiently utilized.

The invention aims at avoiding this disadvantage and, moreover, has as its object to make available not only albumin fractions (PPL) that are free of prekallikrein activator activity, but also other plasma fractions that, in addition to being free of prekallikrein activator activity, are free of prekallikrein burst active and ileum contracting substances, too; thus, they are not to develop pharmacologically negative side effects when applied and, moreover, are to be producible with an improved activity and yield.

This object is achieved according to the invention in that $C_1$-esterase inhibitor is added during the production process of the plasma derivative, yet prior to its filling into final containers.

According to a preferred embodiment of the invention, the addition of $C_1$-esterase inhibitor is carried out at a salt concentration of 5 to 200 $Na^+$ mequ/l, preferably 10 to 50 $Na^+$ mequ/l, and in a pH range of 5 to 9. It has proved that the addition of $C_1$-esterase inhibitor enables a better utilization of the inhibitor at the formation of the complex PKKA/$C_1INA$ with a lower salt concentration. A further preferred embodiment of the production of albumin preparations consists in that the final containers, after having been filled with the product, are subjected to a thermal virus inactivation for 10 hours at 60° C. This embodiment is based on the surprising finding that—although the $C_1$-esterase inhibitor is thermally unstable—the complex compound of prekallikrein activator with $C_1$-esterase inhibitor is thermally stable and resists thermal inactivation, usually a thermal inactivation during 10 hours at 60° C. A further preferred embodiment consists in that the added $C_1$-esterase inhibitor itself is virus-inactivated.

The assay methods with respect to the freedom from side effects of the plasma derivatives produced according to the invention are to be performed as follows:

Determination of prekallikrein activator:

1. Method:

From a purified prekallikrein preparation (PKK) kallikrein (KK) is generated by means of a prekallikrein activator (PKKA). Kallikrein amidolytically cleaves p-nitroanilide (pNA) from a specific chromogenic substrate. The concentration of pNA is measured photometrically at a wave length of 405 nm.

2. Reagents:

Buffer I: 6.0 g TRIS and 23.38 g NaCl are dissolved in about 500 ml $H_2O$ dist. and adjusted to a pH of 8.0 by dilute HCl and filled up to 1,000 ml with $H_2O$ dist.

Buffer II: 1.81 g TRIS, 1.02 g imidazole and 6.43 g NaCl are dissolved in about 500 ml $H_2O$ dist. and adjusted to a pH of 7.9 by dilute HCl and filled up to 1,000 ml with $H_2O$ dist.

Chromogenic substrate: S 2302 (Kabi) H-D-prolyl-1-phenylalanyl-L-arginin-p-nitroanilid-dihydrochloride.

A 10 m molar aqueous solution is prepared. 25 mg S 2302 in 4.1 ml H₂O dist.

Prekallikrein preparation: The production of the preparation is carried out according to a prescription by Harpel, modified by M.S. Horowitz (New York Blood Center). Human citrated plasma is treated with the help of a DEAE cellulose. The fraction that has not been bound to DEAE cellulose contains the prekallikrein.

Positive control (standard): As standard (=reference value), an albumin preparation of the Bureau of Biologics (BoB) of the Food and Drug Administration, Bethesda, Md. 20205, U.S.A., is used. This preparation contains a prekallikrein activator. The generation of kallikrein by this BoB standard constitutes the reference value 1 and is equated to 100%.

Sample: If necessary, the sample is used in the assay in a dissolved or dilute state.

Assay: In a water bath at a temperature of 37° C.
100 μl prekallikrein preparation
50 μl buffer I
25 μl sample
are pipetted into a plastic tube. After an incubation time of 15 min at 37° C.
300 μl buffer II
50 μl S 2302 substrate
are pipetted. This mixture is introduced into a photometer brought to a temperature of 37° C., and the increase in the optical density per minute ($\Delta$OD/min) at a wave length of 405 nm with a layer thickness of 10 mm was measured. The activity of a sample ($\Delta$OD/min) is expressed factorially—relative to the BoB standard having the number 1—or in percent of the BoB standard.

Determination of spontaneous kallikrein liberation in plasma (burst reaction):

1. Method:
From human plasma kallikrein (KK) is spontaneously (within the first minute) liberated by means of the added sample. Kallikrein amidolytically cleaves pNA from the specific chromogenic substrate S 2302. pNA is measured photometrically at 405 nm.

2. Reagents:
(a) Human plasma from a normal donator collective
(b) Buffer II, chromogenic substrate as described in "Determination of PKKA"
(c) Sample is added to test mixture undilute or in precisely determined dilutions.

In order to be able to better detect the spontaneously generated kallikrein activities, i.e. to lower the detection limits, C₁INA antiserum may be added to human plasma, which neutralizes the main inhibitor of the kallikrein burst activity. Thereby it is achieved that the extent of activity of the burst test is increased. Furthermore, the added sample may contain enzymes that react with the chromogenic substrate itself. This can be opposed by lowering this autoamidolytic activity by certain inhibitors, wherein not even the kallikrein burst activity is affected (e.g. aprotinin, trasylene).

3. Assay:
At 37° C.
0.25 ml human plasma
0.025 ml sample
are pipetted into a plastic tube and incubated for 1 min at 37° C., whereupon
0.25 ml buffer II
0.05 ml chromogenic substrate S 2302
are immediately added, this mixture is introduced into a photometer brought to 37° C. and the increase in the optical density per minute ($\Delta$OD/min) at a wave length of 405 nm with a 10 mm layer thickness is measured.

Determination of hypotensively active substances at the isolated guinea pig ileum:

1. Method:
From human plasma, substances that produce reactions on the smooth muscles are liberated by means of sample to be tested (Handbook of Experimental Pharmacology, Ed. E. G. Erdös, Vol. XXV, Springer 1970). In order that the liberated reactive substances will not be degraded, thus evading being tested at the ileum, a suitable kininase inhibitor (e.g. D-3-mercapto-2-methylpropionyl-L-prolin) is added to the reaction mixture.

2. Assay:
An isolated guinea pig ileum having a length of 20 mm and a diameter of 5 mm is introduced into a 10 ml organ bath (modified according to Schulz-Dahle) and calibrated as to its contractability by means of about ten subsequent histamine additions of 5 ng histamine each. Thereafter, the ileum is washed free from histamine.

In a water bath at 37° C. a reaction mixture according to the following pipetting sequence is prepared:
100 μl human plasma
250 μl D-3-mercapto-2-methylpropionyl-L-prolin corresponding to 2 μg
440 μl sample to be tested
are mixed and incubated for 10 min at 37° C. Subsequently, this reaction mixture is applied onto the ileum in the organ bath. If reactive substances are liberated by the added sample, the ileum will contract. As the measure for the contraction, the amplitude that is reached within 30 s after the addition of the reaction mixture onto the ileum is measured in millimeters, the calibration being fixed at 0.315 mN per mm of amplitude with a measurement amplification of 5 mV over a scale length of 250 mm.

The method according to the invention is going to be explained by the following examples.

EXAMPLE 1

Preparation of an albumin fraction:

8% ethanol are added to 10 l human blood plasma at a pH of 7.0 and a temperature of −2° C., a precipitate containing fibrinogen depositing. After separation of this precipitate the ethanol concentration was raised to 25% and the temperature was lowered to −6° C. The precipitate depositing, which contains immune globulin, is separated and the ethanol concentration of the supernatant is raised to 40% at a pH of 6.5 and a temperature of −8° C.

The formed precipitate is separated and discarded. The pH of the supernatant is adjusted to 5.4 at the same temperature, with albumin precipitating. The latter is separated by centrifugation and subjected to a further step of purification: the precipitate is dissolved in water and the ethanol concentration is adjusted to 10% at a pH of 4.8 and a temperature of −2° C. The precipitated globulin is separated and discarded. The ethanol concentration of the supernatant is increased to 40%, the temperature is lowered to −8° C. and the pH is adjusted to 5.1.

The albumin precipitate is collected by centrifugation and, if desired after intermediate lyophilization, is further treated according to the invention in the following manner:

The albumin concentrate is dissolved in NaCl solution, a 4.3% protein solution having a pH of 6.9 and a salt concentration of 140 mequ $Na^{30}/l$ being obtained.

Portions of the solution are admixed with C₁INA in order to obtain a concentration series of
1. 0.01 U C₁INA per g protein

|  | PKKA content in % of BoB standard | Burst reaction 1,000 ΔOD/min | Ileum reaction in mm of contraction amplitude |
|---|---|---|---|
| Heated at 60° C. for 10 hours |  |  |  |
| Albumin solution unheated | 210 | 27 | 0 |
| Albumin solution with 0.01 U C₁INA/g protein | 24 | 5 | 0 |
| Albumin solution with 0.1 U C₁INA/g protein | 0.6 | 2 | 0 |
| Albumin solution with 1.0 U C₁INA/g protein | 0 | 0 | 0 |

2. 0.1 U C₁INA per g protein
3. 1.0 U C₁INA per g protein
4. 10.0 U C₁INA per g protein.

The mixtures remain standing at room temperature for about 24 hours. Thereafter, stabilizing agents (Na-caprylate and Na-acetyl tryptophanate) are added to the solutions in a conventional manner, they are sterile filtered and heated at 60° C. for 10 hours. A parallelly treated albumin sample of the same batch without addition of C₁INA serves as reference.

One unit of C₁ inhibitor (U) corresponds to the amount of C₁ inhibitors contained in 1 ml of fresh plasma.

|  | PKKA content in % of BoB standard | Burst reaction 1,000 ΔOD/min | Ileum reaction in mm of contraction amplitude |
|---|---|---|---|
| Heated at 60° C. for 10 hours |  |  |  |
| Albumin solution unheated | 119 | 19 | 55 |
| Albumin solution without C₁INA addition | 68 | 18 | 22.5 |
| Albumin solution with 0.01 U C₁INA/g protein | 64 | 14 | 21.3 |
| Albumin solution with 0.1 U C₁INA/g protein | 43 | 10 | 21 |
| Albumin solution with 1.0 U C₁INA/g protein | 4 | 0 | 0 |
| Albumin solution with 10.0 g U C₁INA/g protein | 0 | 0 | 0 |

EXAMPLE 2

Preparation of an albumin fraction:

An albumin fraction resulting from the alcohol fractionation—as described in Example 1—is dissolved in an aqueous solution, a solution of 5% protein content and a Na⁺ concentration of about 10 mequ/l being obtained. The pH of the solution amounts to 7.2.

This solution is admixed with C₁INA in order to obtain a concentration series of
1. 0.01 U C₁INA/g protein
2. 0.1 U C₁INA/g protein
3. 1.0 U C₁INA/g protein
4. 10.0 U C₁INA/g protein.

The mixtures remain standing at 37° C. for about 24 hours, are then admixed with stabilizing agents as in Example 1, brought to a Na⁺ concentration of 130 to 160 mequ/l, sterile filtered and heated at 60° C. for 10 hours.

EXAMPLE 3

Preparation of an immune globulin fraction:

8% ethanol is added to 10 l of human blood plasma at a pH of 7.0 and a temperature of −2° C., a precipitate containing fibrinogen depositing. After separation of this precipitate, the ethanol concentration is raised to 25% and the temperature is lowered to −6° C. The precipitate depositing, substantially comprised of immune globulin, is suspended in a phosphate acetate buffer and is admixed with 12% ethanol at a pH of 5.3 and a temperature of −2° C. The precipitate depositing, which contains α and β globulin, is discarded; then, the ethanol concentration of the supernatant is increased to 25% at a pH of 7.0 and a temperature of −6° C., whereby immune globulin is precipitated. The thus obtained immune globulin is collected, if desired lyophilized, and further treated according to the invention in the following manner:

The solution, which has a protein content of 12.5% under physiologic saline and pH conditions, is admixed with C₁INA so that a ratio of
1. 0.01 U C₁INA/g protein
2. 0.1 U C₁INA/g protein
3. 1.0 U C₁INA/g protein
4. 10.0 U C₁INA/g protein
will result. The mixtures are maintained at +4° C. for about 24 hours, are sterile filtered and filled into containers.

|  | PKKA content in % of BoB standard | Burst reaction 1,000 ΔOD/min | Ileum reaction in mm of contraction amplitude |
|---|---|---|---|
| Immune globulin without C₁INA addition | 3,600 | 204 | 88.8 |
| Immune globulin with | 2,300 | 154 | 72.5 |

| | PKKA content in % of BoB standard | Burst reaction 1,000 ΔOD/min | Ileum reaction in mm of contraction amplitude |
|---|---|---|---|
| 0.01 U C₁INA/g protein Immune globulin with 0.1 U C₁INA/g protein | 2,200 | 151 | 50 |
| Immune globulin with 1.0 U C₁INA/g protein | 130 | 9 | 0 |
| Immune globulin with 10.0 U C₁INA/g protein | 0 | 0 | 0 |

EXAMPLE 4

Preparation of an immune globulin fraction:

An immune globulin fraction prepared as in Example 3 and having a protein content of 5.03% is adjusted to
1. 0.01 U $C_1$INA/g protein
2. 0.1 U $C_1$INA/g protein
3. 1.0 U $C_1$INA/g protein
4. 10.0 U $C_1$INA/g protein, sterile filtered, filled into containers and incubated at 37° C. for 24 hours.

| | PKKA content in % of BoB standard | Burst reaction 1,000 ΔOD/min | Ileum reaction in mm of contraction amplitude |
|---|---|---|---|
| Immune globulin without C₁INA addition | 180 | 7 | 42.5 |
| Immune globulin with 0.01 U C₁INA/g protein | 160 | 5 | 22.5 |
| Immune globulin with 0.1 U C₁INA/g protein | 86 | 0 | 7.5 |
| Immune globulin with 1.0 U C₁INA/g protein | 5 | 0 | 3,8 |
| Immune globulin with 10.0 U C₁INA/g protein | 0 | 0 | 0 |

EXAMPLE 5

Preparation of a factor VIII fraction:

46 l of fresh frozen plasma are thawed at 0° C. to +4° C. The cryoprecipitate formed is separated by centrifugation and dissolved in 960 ml 0.1% trisodiumcitrate at 37° C. 8% polyethyleneglycol 2000 are added at a pH of 6.3. Thus, a precipitate forms, which is separated by centrifugation and discarded. By the addition of 12% ethanol to the supernatant at −3° C. the enriched factor VIII is precipitated. After separation it is dissolved in a physiologic buffer and, if desired after intermediate lyophilization, is further treated according to the invention:

From the solution, which has a protein concentration of 1.8% protein, a concentration series of
1. 0.01 U $C_1$INA/g protein
2. 0.1 U $C_1$INA/g protein
3. 1.0 U $C_1$INA/g protein is prepared by the addition of $C_1$INA. The mixtures remain standing at +4° C. for about 24 hours; thereafter, it is sterile filtered and a ready-made product is prepared.

| | PKKA content in % of BoB standard | Burst reaction 1,000 ΔOD/min | Ileum reaction in mm of contraction amplitude |
|---|---|---|---|
| Factor VIII preparation without C₁INA addition | 64 | 71 | 35 |
| Factor VIII preparation with 0.01 U C₁INA/g protein | 34 | 62 | 27.5 |
| Factor VIII preparation with 0.1 U C₁INA/g protein | 12 | 23 | 5 |
| Factor VIII preparation with 1.0 U C₁INA/g protein | 0 | 18 | 5 |

In the further examples it is illustrated that viruses other than hepatitis virus also are inactivatable during the production of albumin preparations within the scope of the method according to the invention.

EXAMPLE 6

From an albumin fraction, a 5% plasma protein solution is prepared. The Na⁺ concentration of this solution is 140 mequ $Na^{30}$/l, the pH being 6.9. This solution is admixed with stabilizing agents (Na-caprylate and Na-acetyltryptophanate). At the same time, $C_1$-esterase inhibitor is added in such an amount that a content of 13 units of $C_1$INA/g protein will result. The thus prepared mixture is sterile filtered and subsequently is admixed with polio virus type I. Then, a thermal inactivation takes place at 60° C. for 10 hours. For control purposes, a plasma protein solution admixed with polio virus type I remains at +4° C. for 10 hours. The control sample and the thermally treated solution are subjected to a virus titer determination. The values given in the following table are decadic logarithms of $TCID_{50}$ per 0.1 ml, $TCID_{50}$ indicating that 50% of the tissue culture preparations exhibit a cytopathogenic effect.

TABLE

| Virus titer of control | >9 |
|---|---|

TABLE-continued

| | Virus titer of sample treated at 60° C. for 10 hours | <1 |
|---|---|---|

EXAMPLE 7

From an albumin fraction a 5% and a 20% protein solution are prepared. The Na+ concentration of both solutions is adjusted to 150 mequ/l, the pH amounting to 7.0. As described in Example 6, the solutions are admixed with stabilizing agents and $C_1$INA and subjected to sterile filtration. Thereafter, the 5% and the 20% protein solutions are admixed with polio virus type I, rotavirus, canine hepatitis virus and Coxsackie virus and are subjected to a thermal inactivation at 60° C. for 16.5 hours. For control purposes, samples admixed with virus remain at +4° C. for the same time. The assessment of virus destruction is effected as in Example 6.

TABLE

| | Polio Type I | Rota virus | Canine hepatitis | Coxsackie |
|---|---|---|---|---|
| 16.5 hrs at 60° C. | | | | |
| Control | 6.6 | 5.6 | 5.4 | 6.6 |
| 5% protein solution | <1 | <1 | <1 | <1 |
| 20% protein | <1 | <1 | <1 | <1 |

TABLE-continued

| | Polio Type I | Rota virus | Canine hepatitis | Coxsackie |
|---|---|---|---|---|
| solution | | | | |

What we claim is:
1. In a method for the production of therapeutically administrable plasma derivatives filled in final storage containers, which are free of prekallikrein activator, hypotensively active constituents and other undesired pharmacologically active substances, by stepwise enrichment of plasma protein and sterile filtration, said method comprising adding $C_1$-esterase inhibitor during the production process of said plasma derivatives to form a thermally stable PKKA/$C_1$INA complex, filling said plasma derivatives in final storage containers, and subjecting said plasma derivatives filled in final storage containers to a thermal virus inactivation treatment.
2. A method as set forth in claim 1, wherein said addition of $C_1$-esterase inhibitor is carried out at a Na+ concentration of 5 to 200 mequ/l and in a pH range of 5 to 9.
3. A method as set forth in claim 2, wherein said Na+ concentration is 10 to 50 mequ/l.
4. A method as set forth in claim 1 wherein said plasma derivative is an albumin preparation, and wherein the thermal virus inactivation is conducted at 60° C. for 10 hours after filling said albumin preparation into said final containers.
5. A method as set forth in claim 1, wherein said $C_1$-esterase inhibitor added itself is virus inactivated.

* * * * *

UNITED STATES PATENT AND TRADEMARK OFFICE
CERTIFICATE OF CORRECTION

PATENT NO. : 4,608,254
DATED : August 26, 1986
INVENTOR(S) : Anton Philapitsch and Yendra Linnau It is certified that error appears in the above-identified patent and that said Letters Patent is hereby corrected as shown below:

Column 2, line 68, "phenylalanyl-L-arginin-p-nitroanilid-dihydrochloride" should read -- phenylalanyl-L-arginin-p-nitroanilide-dihydrochloride.

Column 4, line 68, "$Na^{30}/1$" should read -- $Na^+/1$ --.

Column 8, line 52, "$Na^{30}/1$" should read -- $Na^+/1$ --.

Signed and Sealed this

Fifteenth Day of September, 1987

*Attest:*

DONALD J. QUIGG

*Attesting Officer*   *Commissioner of Patents and Trademarks*